United States Patent [19]

Oehler

[11] Patent Number: 5,285,677
[45] Date of Patent: Feb. 15, 1994

[54] SELECTIVE GAS DETECTION BY FIELD SEPARATION AND VELOCITY OF SOUND DETERMINATION, ESPECIALLY $O_2$ DETECTION

[76] Inventor: Oscar Oehler, Streulistrasse 24, 8032 Zürich, Switzerland

[21] Appl. No.: 720,788
[22] PCT Filed: Nov. 30, 1990
[86] PCT No.: PCT/CH90/00277
 § 371 Date: Jun. 17, 1993
 § 102(e) Date: Jun. 17, 1993
[87] PCT Pub. No.: WO91/09306
 PCT Pub. Date: Jun. 27, 1991

[30] Foreign Application Priority Data

Dec. 8, 1989 [CH] Switzerland ............... 04406/89

[51] Int. Cl.⁵ ......................................... G01N 29/18
[52] U.S. Cl. ................................. 73/24.01; 73/24.02
[58] Field of Search ............... 73/24.01, 24.02, 25.02

[56] References Cited

U.S. PATENT DOCUMENTS

| | | | |
|---|---|---|---|
| 3,347,087 | 10/1967 | Engelhardt et al. | 73/24.01 |
| 4,003,242 | 1/1977 | Houben et al. | 73/24.01 |
| 4,007,625 | 2/1977 | Houben et al. | 73/24.01 |
| 4,280,183 | 7/1981 | Santi | 364/497 |
| 4,848,924 | 7/1989 | Nuspl et al. | 374/119 |
| 5,141,331 | 8/1992 | Oehler et al. | 73/24.01 X |

FOREIGN PATENT DOCUMENTS

| | | | |
|---|---|---|---|
| 56-147027 | 11/1981 | Japan . | |
| 63-83625 | 4/1988 | Japan . | |
| 449286 | 2/1974 | U.S.S.R. | 73/24.01 |
| 2203247A | 12/1988 | United Kingdom . | |
| 2203247 | 12/1988 | United Kingdom . | |

OTHER PUBLICATIONS

Oehler, O., et al., *Photothermal Spectroscopy and Calorimetry by Ultrasonics*, Springer Series in Optical Sciences, vol. 62, Photoacoustic and Photothermal Phenomena II, ED. Murphy et al.; (1990), pp. 519-521.
Oehler, O. et al., *Measurement of Small Temperature Variations in Gas by Ultrasonics*, Helvetica Physica Acta, vol. 61, Pub. Birkhäuser Verlag, (1988), pp. 885-888.
Oehler, O. et al., *A Calorimeter Based on Ultrasonics*, Herbsttagung der SPG/SSP, vol. 63, (1990), pp. 533-534.
Oehler, O. et al., *A Mechanically Tuned Ultrasonic Calorimeter*, Helvetica Physica Acta, vol. 63, p. 829, (1990).
Profos, P., *Handbuch der industriellen Messtechnik*, Essen, (1974), pp. 582-592.
Grice, H. W., et al., "Performance and Applications of an Ultrasonic Detector for Gas Chromatography".
Oehler, O., et al., "Optical Calorimetry Based on an Ultrasonic Resonator".

Primary Examiner—Hezron E. Williams
Assistant Examiner—Joseph W. Roskos
Attorney, Agent, or Firm—Walter C. Farley

[57] ABSTRACT

A method and apparatus for selective detection of gases and vapors uses paramagnetic and electric dipole moments. An inhomogeneous magnetic field (31, 32, 33, 33') or an inhomogeneous electric field (41, 42, 43, 43', 44, 44') through the gas sample causes molecule enrichment in the acoustically sensitive range (34) of an ultrasonic resonator (1). The ultrasonic resonator has mutually opposed ultrasonic transducers operating as a transmitter (2) and a receiver (3). Because of the change in acoustic velocity, the molecule enrichment causes detuning of the ultrasonic resonator (1) and hence a change in signal at the receiving transducer (3). The method is particularly sensitive to the detection of oxygen.

17 Claims, 2 Drawing Sheets

SELECTIVE GAS DETECTION BY FIELD SEPARATION AND VELOCITY OF SOUND DETERMINATION, ESPECIALLY O2 DETECTION

FIELD OF THE INVENTION

The invention is in the field of gas sensors. It relates to a process and an apparatus for selectively measuring gases and vapors, in particular oxygen.

There is an increasing need for detecting gases selectively and reliably. On one hand the measurement of gases, in particular harmful compounds, represents an important field for ecologic investigations. In addition in medical techniques the measurement of gas concentrations is of increasing importance e.g. in connection with the respiration control.

There exist several methods for the selective detection of gases. The solid state sensors are very much worth their price, but usually they do not represent a very selective method. Those sensors partly are based on catalytic combustion, in which heat production (pellistor) or the creation and diminution of oxygen vacancies, respectively, are measured. Of great importance are the gas sensors based on field effect transistors which are equipped with a gas sensitive gate electrode. In addition chemical sensors are important where the ionic conduction of an electrolyte is used. In those cases, solubility of the gas in the electrolyte is required. The lambdaprobe, an important part in catalysator-equipped cars, is based on the high temperature solubility of oxygen in zirconium oxide and the corresponding conductivity of oxygen ions.

Optical gas sensors are characterized by their high selectivity and sensitivity. The optical emission capability of gases allows their detection even at extremely low concentrations.

Many gases and vapors can be detected by using the property of selective absorption of infrared radiation. For this reason there are a number of instruments on the market which are based on an extinction measurement in the infrared. Further, gases can be detected very reliably and selectively by utilizing the photoacoustic effect. The latter is based on a microphonic measurement of the gas pressure which is produced on the absorption of intensity-modulated infrared radiation. However, it has to be mentioned that when accomplishing photoacoustic measurements the acoustical disturbance given by the measuring principle can never be prevented completely.

The most important condition for using a detection process based on infrared spectroscopy is the absorption capability of the gas in this radiation range. Most gases and vapors have a very characteristic spectrum in the middle infrared, being produced by changes of the dipole moment on molecular-internal vibrations. However, monatomic gases, as well as homo-molecular two-atomic gases like $N_2$ and $O_2$ are not susceptible to infrared spectroscopic investigations. In particular, oxygen is very important in medical analysis and in heating techniques (control of heating installations).

Several possibilities are available for detecting oxygen selectively. Those processes which are based on the paramagnetic property of oxygen have proven very useful. While most gases are very weakly diamagnetic (the susceptibility is of the order of $(-0.5 \cdot 10^{-9}$ SI units), oxygen is characterized by a high paramagnetic susceptibility of $+107.8 \cdot 10^{-9}$ SI units as compared with NO ($+48.7 \cdot 10^{-9}$ SI-units) and $NO_2$ ($+3.3 \cdot 10^{-9}$ SI units).

Conventional methods using the paramagnetism of oxygen for its selective detection are based e.g. on the temperature dependence of the magnetic susceptibility. Corresponding to the Curie law in so-called thermomagnetic devices the susceptibility of gas samples at two different temperatures are compared. The detection is based on a gas flow measurement, the so-called magnetic wind, which arises between the gas samples of different temperatues. Those devices are relatively slow because they are based on a thermal effect. In addition there is a position dependence of the sensor because of the disturbance by convective air flow. Although the paramagnetism is a specific property of oxygen, there exists an additional cross sensitivity with other gases because of the heat conductivity of gas mixtures.

An additional and well established process for the selective detection of oxygen is based on the magneto-mechanical principle: To employ this process, two small glass balls usually are connected as a small, symmetrical dumbbell and are arranged in an inhomogeneous magnetic field. An oxygen containing, paramagnetic gas mixture is attracted by the inhomogeneous magnetic field. The glass balls either are evacuated or contain a diamagnetic gas and therefore exhibit negative buoyancy in an inhomogeneous magnetic field and in the presence of oxygen. The buoyancy acts on the dumbbell, which is suspended on a torsion thread, and produces a torque. The deviation is measured mechanically and is proportional to the buoyancy and therefore to the oxygen concentration of the gas. These instruments show good linearity. Their response time is about 5 sec, an acceptable value for most applications for clinical surveillance of the respiration. Because of their sensitive mechanics, those instruments are relatively expensive and subject to mechanical disturbance.

Commercially meaningful are further oxygen detecting instruments which operate according to the magneto-pneumatic principle. The detecting is based on a pressure rise, occurring in an oxygen containing measuring gas in a magnetic field. Since the pressure rise of about $10^{-4}$ mbar is relatively small, a subtle method for measuring the pressure is required. The pressure difference can be determined e.g. by the velocity of a gas flow. In this case a comparing measurement with a reference gas is required. Another possibility is based on the measurement of the pressure difference which is induced by the modulation of a magnetic field by means of a microphone. In this case the typical temporal resolution of respiration processes of 0.1 sec can be reached approximately at a $t_{90}$-value of 0.15 sec. Because of the required minimum volume of 20 $cm^3$ an even shorter response time hardly can be realized.

In conclusion, it can be pointed out that several methods have been developed on the basis of the paramagnetic property which allow selective and reliable detection of oxygen. Common to all of these methods is that the realization of corresponding apparatus requires great effort. Because of the smallness of the effect there is a large disturbance in connection with the position of the sensor, its temperature etc. In addition the required temporal resolution cannot, or only barely, be reached.

SUMMARY OF THE INVENTION

An object of the invention is to offer a process and a corresponding apparatus for selectively detecting gases and vapors on the basis of their magnetic or electric dipole momentum.

This object is achieved by separating paramagnetic or electric dipole moments containing molecules of a mixture of gaseous media in an anisotropic, non-stationary magnetic or electric field, respectively, and by detecting the changes of the gas or vapor concentration by changes of the velocity of sound. The latter quantity is measured in particular by the detuning of an ultrasonic resonator.

It is well known that paramagnetic molecules, like oxygen, get attracted in an anisotropic field because of their magnetic momentum. Additionally it is obvious that molecules having an electric dipole moment, like water vapor, get attracted by an anisotropic electric field.

The described magneto-mechanical oxygen detecting devices are based on the buoyancy force of paramagnetic molecules in the anisotropic magnetic field. Further it has to be assumed that there is a concentration of corresponding gas components at the influence of the inhomogeneous magnetic field. But, first, it seems to be completely absurd to use this effect for detecting paramagnetic or electric dipole moment attributed gases. If there would not be a very small enrichment effect, the buoyancy in an inhomogeneous magnetic field would show a nonlinear dependence of the oxygen concentration. But as given in "Handbuch der industriellen Messtechnik" (Handbook of Industrial Measuring Techniques), Essen (1974) by P. Profos, indicators for magnetomechanical oxygen detecting instruments are strictly linear displays.

In addition a simple estimation of the oxygen enrichment effect in air leads to an extremely small result:

In the mentioned handbook of industrial measuring techniques it is stated at page 587 that the torque acting on the glass ball dumbbell in magneto-mechanical instruments is of the order of $10^{-10}$ Nm. From typical geometric data of the dumbbell (distance between the balls is 6.6 mm and each has a diameter of 2 mm) it follows that, at a oxygen concentration of 20%, a force of $F=7\cdot10^{-25}$N acts at a single oxygen molecule in the inhomogeneous magnetic field. Similar force values of $F=9.75\cdot10^{-25}$N are obtained when using the susceptibility of oxygen and assuming the molecule being in an inhomogeneous magnetic field of 0.8 Tesla and an inhomogeneity of 0.27 Tesla/mm.

Assuming this force acting on a single oxygen molecule, the drift velocity $v_d(t)$ can be calculated on the basis of the following formula:

$$v_d(t) = (v(0) - F\cdot B) \exp(-t/(B\cdot m)) + F\cdot B, \quad v_d \approx F\cdot B,$$

wherein B represents the mobility, which latter follows from the diffusion constant according to the formula of Einstein: $B\cdot k\cdot T = D$; k is the Boltzmann constant; and m is the molecular weight of oxygen.

On the basis of the diffusion constant of oxygen $B=0.178$ cm$^2$/sec, a drift velocity of $v_d=4.2\cdot10^{-7}$ cm/sec can be obtained.

This very small value has to be compared with the average thermal velocity of the oxygen molecules at 300° K. of $v=483$ m/s. At first sight it therefore seems to be completely impossible that a measurable separation effect of oxygen can be expected.

However, the drifting of the oxygen molecules into the inhomogeneous magnetic field leads to a local increase of the gas density. Because of the density-dependency of the velocity of sound, a change of the velocity of sound therefore results.

On the basis of my own measurements, the use of an ultrasonic resonator allows the accurate measurement of periodic changes of the velocity of sound. As given in U.S. Pat. No. 5,141,331 and in the articles "Photothermal Spectroscopy and Calorimetry by Ultrasonics" by O. Oehler, S. Friedrich and A. Schäppi in Springer Series in Optical Sciences, 62; "Photothermal and Photoacoustic Phenomena II", 519 (1990); and in "A MECHANICALLY TUNED ULTRASONIC CALORIMETER", O. Oehler, J. Wieland, D. Raillard and M. Schumacher, Helv. Phys. Acta, 63, 829 (1990), periodic temperature changes of $6\cdot10^{-5}$ degrees easily can be detected by using an ultrasonic resonator.

It was found that the ultrasonic resonator shows its highest temperature-sensitivity and therefore also its highest sensitivity to changes of the velocity of sound in a central range of a diameter of 2 mm. The corresponding comment is given in the article "A Calorimeter Based on Ultrasonics" of O. Oehler, P. Rusch and S. Dornbierer, in Helv. Phys. Acta., 63, 533 (1990).

If one assumes that oxygen enters a cylinder (diameter d=2 mm, volume $V=(d/2)^2\cdot\pi\cdot L$) because of its paramagnetic property at a velocity of $v_d=4.2\cdot10^{-7}$ cm/sec, then one obtains in the cylinder, after the time $\Delta t$ and assuming a homogeneous distribution, the following relative change of the density $\Delta\zeta/\zeta$:

$$\Delta\zeta/\zeta = \Delta V/V = v_d\cdot\Delta t\cdot d\cdot\pi\cdot L/(d/2)^2\cdot\pi\cdot L = 4\cdot v_d\cdot\Delta t/d.$$

On using the calculated drift velocity one obtains after one second a relative change of the density of:

$$\Delta\zeta/\zeta = 4\cdot4.2\cdot10^{-7}/0.2 = 8.4\cdot10^{-6}.$$

According to the formula describing the velocity of sound there is when the density changes the following change in the velocity of sound:

from $c = \sqrt{K\cdot p/\zeta}$ where $K = c_v/c_p$, the ratio of specific heat, $\Delta c = -(c/2)\cdot\Delta\zeta/\zeta$.

Numerically this is:

$$\Delta c = 1.34\cdot10^{-3} \, m/s$$

At an O$_2$-concentration of 20%, the measurements showed:

$$\Delta c = 6.8\cdot10^{-4} \, m/s$$

On the basis of the mentioned temperature sensitivity of the ultrasonic resonator of 60 μK and corresponding to the temperature sensitivity of the velocity of sound of 0.6 m/sec one obtains a velocity of sound sensitivity of the apparatus of:

$$\Delta c = 3.6\cdot10^{-5} \, m/s.$$

Like the experiment, the calculations also show good measurability of the effect.

It has to be mentioned that the given calculations represent a crude estimation, but nevertheless prove the utility of the process to measure the oxygen enrichment in an inhomogeneous magnetic field by means of the change of the velocity of sound.

An additional allusion to the measurability can be found from the considerable difference between the velocity of the sound of air being 331 m/sec and that of oxygen being 316 m/sec of 15 m/sec. A change of oxygen concentration in the velocity of the sound-sensitive range of the ultrasonic resonator therefore influences the velocity of sound in the oxygen-nitrogen mixture.

The determination of the oxygen content of oxygen-nitrogen in a mixture could surely be accomplished directly by using the difference of the velocity of sound of the two gases—and without the separation of the two components in an inhomogeneous magnetic field. But it has to be pointed out that the selectivity of the oxygen measurement then would be lost. The presence of water vapor or carbon dioxide, for example, influences the velocity of sound too. Furthermore, a direct measurement of the velocity of sound via its temperature dependence would induce a high gas temperature-dependence of the measurement.

Since the method presented here measures only magnetic field-induced changes of the velocity of sound, the selectivity and the temperature independence are largely guaranteed. There is only a cross-sensitivity with respect to nitric oxides because these gases are also paramagnetic. In principle, it would be possible to measure NO and $NO_2$ in the absence of oxygen by this method.

The detectability of oxygen in an inhomogeneous magnetic field by means of using an ultrasonic resonator found experimental confirmation. The oxygen content of the air can be detected easily by this method.

BRIEF DESCRIPTION OF THE DRAWINGS

Examples of possible constructions of adequate instruments are shown in the following drawings wherein.

DESCRIPTION OF THE PREFERRED EMBODIMENTS

Figure 1:
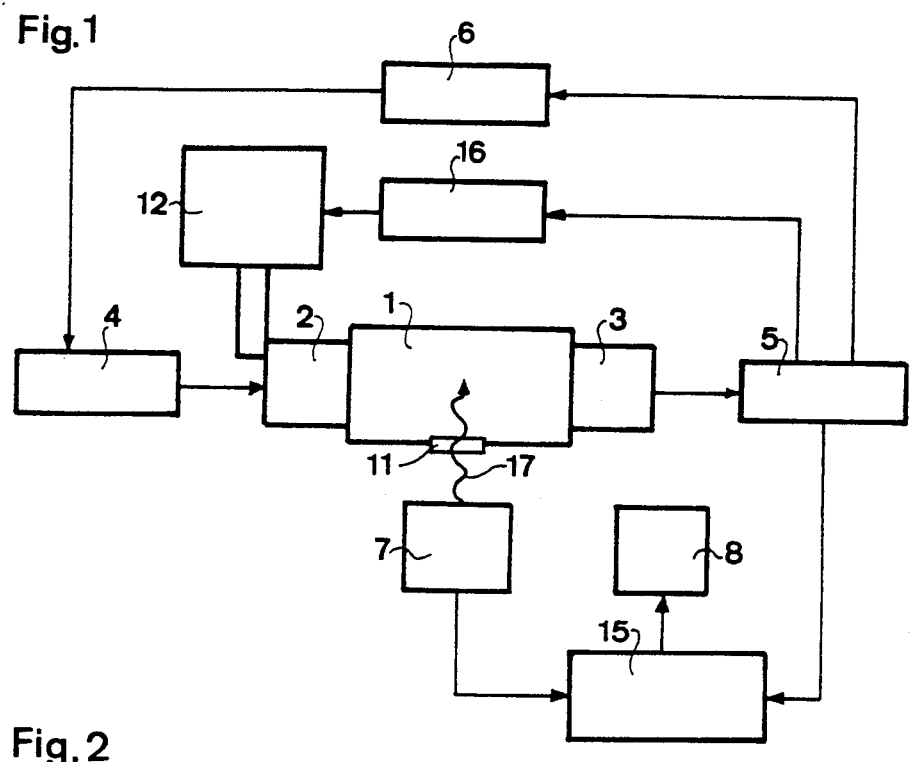
FIG. 1 is a schematic block diagram of a known construction of an ultrasonic resonator for measuring temperature variations caused by absorption of light.

FIG. 1 shows the construction of an aforementioned ultrasonic means for measuring small temperature fluctuations in a gas caused by infrared radiation absorption. The gas temperature measuring method is based on the large temperature dependence of the sonic velocity of gases. The velocity is measured by means of an ultrasonic field, mainly in the form of an acoustic resonator 1. The acoustic resonance builds up between the ultrasonic transducer pair comprising an ultrasonic transmitter 2 and an ultrasonic receiver 3.

The ultrasonic transmitter 2 is excited by a generator 4 at a frequency of typically several hundred kHz. The generator signal can be sinusoidal or can, for example, comprise a regular train of rectangular pulses. At receiver 3 appears a signal, whose peak-to-peak value is dependent on the tuning of the resonator 1, apart from the sensitivity of the receiver 3 and the sound absorption in the resonator chamber 1.

The receiver signal is supplied to a device 5, referred to hereinafter as the analyzer. This device 5 either analyses the peak-to-peak value of the signal received, or it determines the phase position of the signal with respect to the input signal at the transmitter 2. This analysis of the signal supplied by the receiver 3 is e.g. based on a peak-to-peak measurement, a rectification with following smoothing, a phase detection or a phase-sensitive amplification by means of a lock-in amplifier.

By the choice of the frequency and the length of the resonator in the case of a peak-to-peak analysis, it is appropriate to operate the ultrasonic resonator in one resonance flank. For phase detection, the resonator is advantageously operated at the resonance maximum, e.g. in the maximum phase change range. It is also advantageous to choose a high ultrasonic frequency due to the substantial proportionality of the peak-to-peak rise to the frequency.

The upper limit of the ultrasonic frequency is given by the sound absorption capacity of the specimen gas, which rises sharply with increasing frequency above 100 kHz. However, it is pointed out that the frequency can be made higher than is possible with commercial air-adapted ultrasonic transducers (50 to 220 kHz). Thus, in the present case the sound signal does not have to be efficiently transmitted over a distance of several meters or decimeters, such as is normally desired and instead it only has to be transmitted in the millimeter range.

By operating the ultrasonic resonator on a resonance flank in peak-to-peak analysis, or in the resonance maximum for phase detection, as well as by the choice of a high frequency, it is ensured that the temperature-caused change in the tuning has a maximum effect on the output signal of the analyzer 5.

The change of the resonator tuning can be gathered directly from the change to the signal envelope, i.e. the quasi-direct current value or phase displacement at analyzer 5. However, it is pointed out that in both cases the linear temperature measuring range is very limited. However, as only small temperature fluctuations are to be measured, this restriction is not serious. However, slow drift-like temperature changes can bring about a drift in the resonator tuning and therefore a change in the temperature sensitivity. Therefore ways must be sought for effectively counteracting large, long-term effects.

For example, the ultrasonic frequency can be followed up in such a way that the resonator tuning, i.e. the peak-to-peak value at the receiver 3 remains constant. To this end, e.g. the output signal of the analyzer 5 can be supplied as a control signal via a suitable regulator 6 to a voltage-controlled generator 4. The coverable temperature measuring range is given by the operating range of the ultrasonic transducers. Typically, with ultrasonic transducers 2, it is possible to cover the desired frequency ranges of 1 to 2%.

However, a randomly large temperature range can be obtained if the resonator 1, instead of being tuned electrically, is tuned by means of a regulator 16 and a mechanical shifting device 12 by modifying the spacing between the ultrasonic transducers. However, it is pointed out that in this case the tuning is relatively complicated. In particular, the precision requirement on the mechanical construction is considerable. For example, the Q factor of the ultrasonic resonator i drops significantly if the surface of the ultrasonic transducers 2, 3 are not maintained precisely parallel.

It is also conceivable to combine both tuning types of the ultrasonic resonator, i,e. the mechanical and electrical tuning types. This situation is shown in FIG. 1. For example, the coarse tuning can be carried out mechanically with the aid of a corresponding regulator 16 and a shifting device 12, while the fine tuning can be carried out electrically by means of a regulator 6 and the voltage-controlled oscillator 4.

Conclusions can be drawn regarding the sonic velocity, and therefore the temperature of the gas in the ultrasonic resonator 1, from the output signal of the analyzer 5 or from the regulating quantity.

Temperature variations in the ultrasonic resonator 1 can be achieved by light and in particular infrared irradiation 17. Small temperature fluctuations in the ultrasonic resonator 1, which are brought about by absorption of intensity modulated radiation and consequently correlated with the light signal, can be measured by means of an analyzer 15 in the form of a lock-in amplifier. The latter uses as a reference the intensity-modulated signal of light source 7. The output signal of analyzer 15 is the measured value sought, which gives information on the light absorption in the ultrasonic resonator. This signal is therefore supplied to a recorder 8, e.g. in the form of a plotter, voltmeter or computer input. The described process makes it possible to measure gas temperature changes in the range of $10^{-4}$ degrees. Further details are provided in the aforementioned articles by O. Oehler, J. Wieland and S. Friedrich.

It would initially not appear to be particularly advantageous to on the one hand use the output signal of analyzer 5 for further analysis in the lock-in amplifier 15 and on the other hand to keep this signal at a fixed value, e.g. by means of regulator 6. However, it is obviously desirable to use regulator 6 for compensating slow drift phenomena, so that the lock-in amplifier 15 measures the rapid, source-synchronous light signals.

Figure 2:
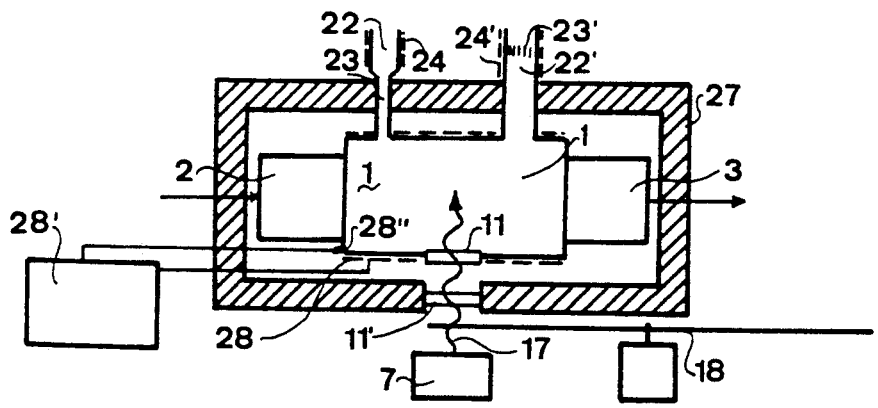
FIG. 2 is a schematic side elevation, in section, of a photothermal gas detection means, particularly of a $CO_2$ detecting apparatus, with modulating and filtering means for the incident light radiation.

FIG. 2 shows a more detailed view of an apparatus for measuring the photothermal effect. The ultrasonic resonator 1 is formed by the two facing ultrasonic transducers 2, 3. The light from source 7 passes through a window 11 into the ultrasonic resonator 1 constructed as a gas cell. There is at least one opening 22, 22' in the gas cell wall for exchanging the gaseous measuring material 21. The openings are optionally provided with flow resistances 23, 23', which can be in the form of valves, pipe constrictions 23, filter plates 23' or gas permeable membranes. It is pointed out that these flow resistances 23, 23' must not have a sound absorbing effect, unlike in the case of photoacoustic measurements at low frequencies, where a good acoustic separation of the cell from the environment is unavoidable. It must merely be ensured, as stated, that external temperature fluctuations have no effect on the ultrasonic resonator 1. There would be no need for light entrance window 11, if it can be ensured that the opening in the ultrasonic resonator leads to no significant gas circulation-caused temperature fluctuations.

For preventing undesired temperature fluctuations in the ultrasonic resonator 1, it is recommended that it be surrounded by a jacket-like thermal insulation 27 and/or optionally to keep it at a constant temperature by means of a heating device 28, a heating control device 28', and a heat sensor 28". It can also be advantageous to bring the gaseous measuring material to the ultrasonic resonator temperature by heating the feed lines with heating elements 24, 24'.

The light source 7 is intensity-modulated, which can be achieved by switching the current on and off, or by means of a light chopper 18, located in the light beam 17 between light source 7 and ultrasonic resonator 1. An optical filter 11' can also be positioned in the light beam 17. The insertion of such a filter is particularly appropriate if the light source has a broad-band spectrum, i.e. if for example the source 7 is a heat emitter. In this case an optical bandpass filter 11' can produce adequate monochromatic radiation, so that a selective light absorption by gases in the cell is ensured.

If the wavelength of the light entering the ultrasonic resonator 1 through window 11 meets the selective spectral absorbing range of gases, the apparatus shown in FIGS. 1 and 2 can be used for selective detection of gases and vapors. However, the sensitivity is not as high as with an apparatus based on the photoacoustic effect, but said apparatus has a nearly negligible fault susceptibility to pressure fluctuations and solid-borne sound. Because of the high selective absorption property of $CO_2$ at 4.3 $\mu$m the described process is mainly suitable for detecting this gas.

Figure 3:
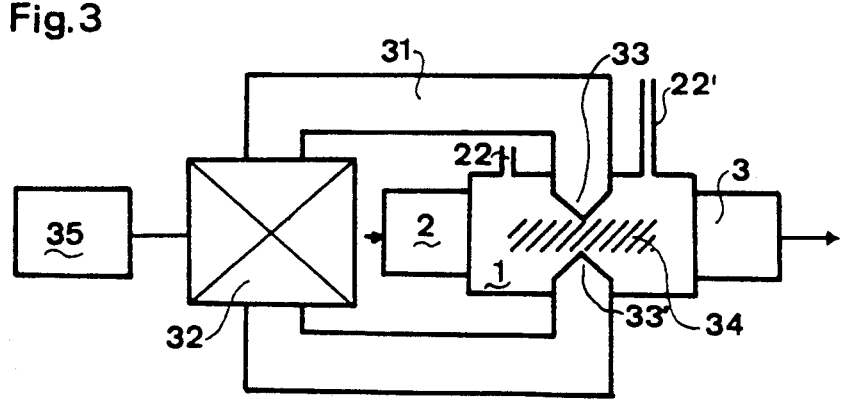
FIG. 3 is a schematic diagram of an example of a corresponding oxygen measuring means including an ultrasonic resonator and an inhomogeneous magnetic field.

FIG. 3 shows an example of the inventive means for selective detection of oxygen and/or other gaseous media having a large paramagnetic susceptibility like NO or $NO_2$. The basis of the apparatus again is the aforementioned ultrasonic resonator 1 as shown in FIGS. 1 and 2, composed of two oppositely arranged ultrasonic transducers 2, 3 and associated controllers 4, 12, regulators 6, 16 and demodulation electronics 5, 15. (For simplicity the latter units are not shown again in FIG. 3). Instead of an intensity modulated light beam 17 acting on the ultrasound sensitive zone 34 of the ultrasonic resonator, a time-variable inhomogeneous magnetic field is established therein. The magnetic field may be produced by means of an electromagnet, composed of a bobbin 32, the core 31 and the pole-pieces 33, 33'. The time-variable, in particular, periodic excitation of the magnet is accomplished via a control unit 35. An output of the unit 35 is connected to a low-frequency-demodulator 15 for supplying the reference signal.

Either in the low frequency demodulator 15 or in the attached recording device 8, as indicated in FIG. 1, linearization of the signal is achieved. This procedure is necessary since the amplitude of the low frequency signal, as mentioned before, is not linearly related to the oxygen concentration.

The inhomogeneity of the magnetic field is defined especially by the shape of the pole-pieces. In order to obtain a high inhomogeneity it is desirable to give them the shape of a tip, as shown in FIG. 3. However it may be preferable to use knife-edge shaped pole-pieces, wherein the edge is parallel to the cylindrical sound sensitive zone 34 of the ultrasonic resonator.

In analogy to the device shown in FIG. 2, the gas to be measured can be supplied by means of the pipes 22, 22', and flow resistors 23, 23' may be installed in the gas pipes 22,22' in order to reduce the gas flow induced temperature fluctuations. An additional thermostating of the supplied gas by means the thermostatic device 24 which is attached at the supply tube 22 is desirable as well as the thermostating of the ultrasonic resonator 1. It was already mentioned in connection with FIG. 2 that for this purpose a thermostatic device 28 can be used. This device, for instance a Peltier element or heating means, may be connected to a control unit 28' which senses the temperature of the ultrasonic resonator housing by a thermic sensor 28". The resonator may, if necessary, be surrounded additionally by heat insulation 27, as shown in FIG. 2. The purpose of the described thermostating means is to reduce thermic disturbances which manifest in the tuning of the ultrasonic resonator 1 via the temperature dependence of the velocity of sound.

An additional disturbance is caused by the gas composition dependence of the velocity of sound. The given measuring process uses only periodic changes of the velocity of sound due to the influence of the magnetic field; however, the change of the velocity of sound by itself induces considerable detuning of the resonator. Our own measurements have shown that the gradient of the resonance curve is constant over a wide range. In this context it may be emphasized by the already cited article by O. Oehler, J. Wieland and S. Friedrich "Measurement of Small Temperature Variations in a Gas by Ultrasonics", Helv. Phys. Acta, 61, 885 (1988). If necessary, because of a very large change of the gas composition, the resonator 1 can be tuned by means of a frequency change at the generator 4 or by mechanical tuning via the mechanical shifting unit 12.

It has to be mentioned that the velocity of sound variations have not necessarily to be measured by means of an ultrasonic resonator 1. It is e.g. possible to detect the change of the velocity of sound by measuring the sound propagation time between the ultrasonic emitter 2 and the ultrasonic receiver 3. Periodic pulses can be delivered by the emitter and be received by the receiver. It is also possible for a single ultrasonic transducer 2 to be operated alternately as an emitter of ultrasonic pulses and a receiver, respectively, whereby the emitted signal would be reflected by a reflector. These two described methods would be conceivable, because the time difference, in our case the time delay between the emitted and the received signal, is measurable very accurately, as is well known.

Figure 4:
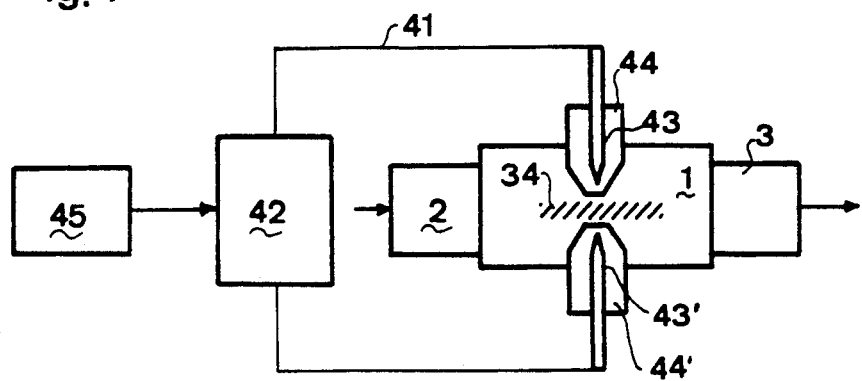
FIG. 4 is a schematic diagram of an apparatus for detecting gases having a high electric dipole moment by means of an ultrasonic resonator and an inhomogeneous electric field.

In analogy to the enrichment of paramagnetic gas molecules in an inhomogeneous magnetic field it is conceivable to enrich gases and vapors which contain a permanent electric dipole moment, by an inhomogeneous electric field. The inhomogeneous electric field may be produced, as shown in FIG. 4, by means of tip- or edge-shaped electrodes 43, 43', which are connected with a high voltage generator 42 via the electric conductors 41. In analogy to the one of FIG. 3, the generator 35 delivers, via the high voltage generator 42, a time-variable, possibly periodic, signal which induces an inhomogeneous, variable electric field in the velocity of sound sensitive region 34 of the ultrasonic resonator 1. For preventing electrical break-throughs at the tips of the electrodes, it may be wise to surround the electrodes by a dielectric covering 44.

The oxygen detecting method shown has the advantage that it can be combined with a $CO_2$ measurement. If in addition to the inhomogeneous magnetic field infrared light of a wavelength of 4.3 μm (the absorption frequency of $CO_2$) is radiated into the ultrasonic resonator, the carbon dioxide concentration of the air also is detectable via the periodic heating.

Figure 5:
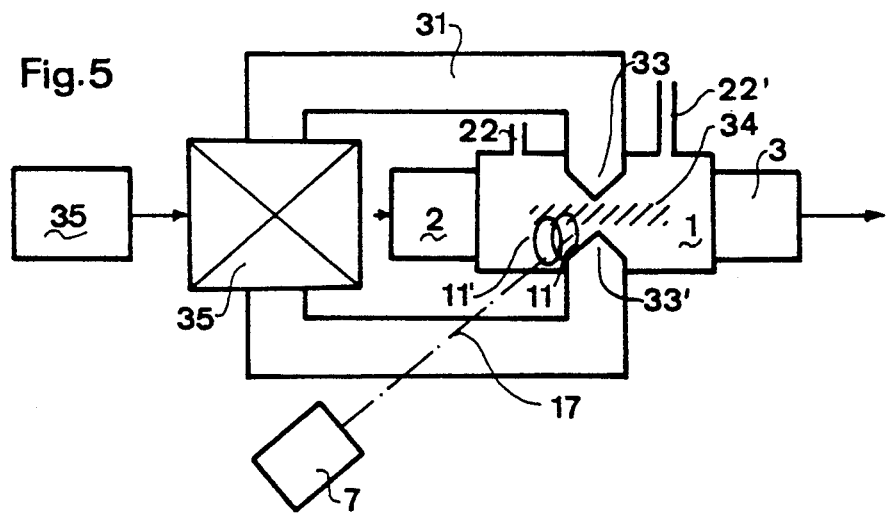
FIG. 5 is a schematic diagram of a combination of an oxygen sensor and a $CO_2$ sensor characterized by simultaneous applyication of an inhomogeneous magnetic field and irradiation of the ultrasonic resonator with infrared light.

FIG. 5 is an example of such a combined apparatus which allows the simultaneous measurement of oxygen and a light absorbing gas, like carbon dioxide. On one hand intensity-modulated light radiates into the velocity of sound sensitive region 34 of the ultrasonic resonator 1 and on the other hand an inhomogeneous magnetic field is established additionally in the region 34 by means of an electromagnet 31 and suitable pole-pieces 33, 33'. The light irradiation and its absorption-induced temperature variations lead to a periodical detuning of the resonator 1, while the periodic magnetic field influences the velocity of sound via a periodic gas enrichment.

The two fields can be applied alternately in which case a single low frequency demodulator 15 is used. It is even possible to detect oxygen and carbon dioxide simultaneously (being very important on monitoring respiration processes) if the inhomogeneous magnetic field and the infrared radiation are modulated at different frequencies. The separation of the two low-frequency signals is accomplished by lock-in detection at the corresponding frequencies. In this case the corresponding signals are obtained via two different low-frequency demodulators 15, 15'.

Like the arrangement described, a combination of the magnetic method, shown in FIG. 3, with the electric method of FIG. 4 is also conceivable.

By using simultaneously a magnetic alternating field and an electric alternating field as well as infrared radiation, it is even possible to detect selectively three gases simultaneously, namely oxygen, carbon dioxide and water vapor. Such a device would be advantageous e.g., for monitoring respiration processes.

In order to simplify the presentation, the thermostat of the ultrasonic resonator 1 was omitted from FIGS. 3, 4, and 5. Such steps, as given in FIG. 2 could, if necessary, be advantageous for decreasing thermally induced disturbances. In addition it may be conceivable that there are means for mechanical tuning—if necessary for coarse tuning—as shown in FIG. 1.

I claim:

1. A method for selective detection of gases and vapors of a gas and/or vapor mixture comprising the steps of
   changing the concentration of the gas or vapor to be measured by subjecting the gas or vapor to an inhomogeneous field,
   transmitting sound through the gas or vapor, and
   detecting the change of the gas or vapor concentration by measuring changes in the velocity of sound transmitted therethrough.

2. A method according to claim 1 wherein the inhomogeneous field is a periodically variable field.

3. A method according to claim 2 wherein the inhomogeneous field is a magnetic field.

4. A method according to claim 2 wherein the inhomogeneous field is an electric field.

5. A method according to claim 1 wherein measuring the velocity of sound is accomplished by measuring the propagation time of a sonic pulse.

6. A method according to claim 1 wherein measuring the velocity of sound is accomplished by measuring detuning of an ultrasonic resonator.

7. A method according to claim 1 wherein the change of the velocity of sound is accomplished by the irradiation of light in addition to changing the concentration of the medium to be measured by an inhomogeneous field.

8. An apparatus for selective detection of gases or vapors of a gas or vapor mixture, comprising
two ultrasonic transducers (2, 3) facing each other and defining a velocity-of-sound sensitive region (34),
electronic means for operating (4, 12), controlling (6, 16) and demodulation (5, 15), and
means (31, 32, 33, 33', 35, 41, 42, 43, 43', 45) for inducing an inhomogeneous field arranged to act on a gas or vapor to be measured which is positioned in the velocity-of-sound sensitive region (34) between said two ultrasonic transducers (2, 3).

9. An apparatus according to claim 8 wherein said transducers include an ultrasonic emitter (2) and an ultrasonic receiver (3), said ultrasonic emitter being connected to said electronic means to emit sonic pulses and said ultrasonic receiver is arranged to receive said pulses after passing through said inhomogeneous field.

10. An apparatus according to claim 8 wherein said transducers include an ultrasonic emitter (2) and an ultrasonic receiver (3), said ultrasonic emitter and ultrasonic receiver being connected with said electronic means and dimensioned and arranged to form an ultrasonic resonator (1).

11. An apparatus according to claim 8 and including an electromagnet (31) having pole-pieces (33, 33') and a magnet coil (32) connected to said electronic means to form an inhomogeneous, periodic magnetic field in said velocity-of-sound sensitive region (34) of said ultrasonic transducers (2, 3), said pole-pieces having ends shaped to form edges pointing toward said region.

12. An apparatus according to claim 11 and further comprising means for generating a light beam, a window (11) and a filter (11') to permit entry of said light beam (17) into said velocity-of-sound sensitive region (34) between said ultrasonic transducers (2, 3).

13. An apparatus according to claim 8 and including a high voltage circuit (41) and electrodes (43, 43') arranged to form an inhomogeneous, periodic electric field in said velocity-of-sound sensitive region (34) of said ultrasonic transducers (2, 3), said electrodes having ends shaped to form edges pointing toward said region.

14. An apparatus according to claim 13 and further comprising means for generating a light beam, a window (11) and a filter (11') to permit entry of said light beam (17) into said velocity-of-sound sensitive region (34) between said ultrasonic transducers (2, 3).

15. An apparatus according to claim 8 and including gas exchange pipes, at least one flow resistance (23, 23') attached in said gas pipes (22, 22'), a first thermostat (24) in one said gas pipe (22), temperature control means for said ultrasonic resonator (1) including a second thermostat (28), a thermal sensor (28") and thermal insulation (27) for reducing thermal disturbances.

16. An apparatus according to claim 8 and including an electromagnet (31) having pole-pieces (33, 33') and a magnet coil (32) connected to said electronic means to form an inhomogeneous, periodic magnetic field in said velocity-of-sound sensitive region (34) of said ultrasonic transducers (2, 3), said pole-pieces having ends shaped to form tips pointing toward said region.

17. An apparatus according to claim 8 and including a high voltage circuit (41) and electrodes (43, 43') arranged to form an inhomogeneous, periodic electric field in said velocity-of-sound sensitive region (34) of said ultrasonic transducers (2, 3), said electrodes having ends shaped to form tips pointing toward said region.

* * * * *